United States Patent [19]

Malek et al.

[11] 4,088,669

[45] May 9, 1978

[54] METHOD FOR PREPARING ORGANOSILICON COMPOUNDS FROM ELEMENTAL SILICON AND HYDROCARBON ETHERS

[75] Inventors: James R. Malek; John L. Speier; Antony P. Wright, all of Midland, Mich.

[73] Assignee: Dow Corning Corporation, Midland, Mich.

[21] Appl. No.: 785,882

[22] Filed: Apr. 8, 1977

[51] Int. Cl.$^2$ .............................................. C07F 7/18
[52] U.S. Cl. ...................... 260/448.8 R; 260/448.2 T
[58] Field of Search ................... 260/448.2 T, 448.8 R

[56] References Cited

U.S. PATENT DOCUMENTS

| | | | |
|---|---|---|---|
| 2,459,539 | 1/1949 | Rochow | 260/448.2 T |
| 3,505,379 | 4/1970 | Bowitz | 260/448.8 R |

FOREIGN PATENT DOCUMENTS

| | | | |
|---|---|---|---|
| 187,342 | 7/1956 | Japan | 260/448.8 R UX |

OTHER PUBLICATIONS

Zuckerman, Technical Report Contract No. NONR-1966(13), Sep. 1960.

*Primary Examiner*—Paul F. Shaver
*Attorney, Agent, or Firm*—George A. Grindahl

[57] ABSTRACT

Organosilicon compounds bearing silicon-bonded hydrocarbon radicals and silicon-bonded hydrocarbonoxy radicals are obtained by contacting activated silicon, a hydrocarbon ether and a halogen-containing catalyst in a closed system at elevated temperature. Silanes and siloxanes, particularly methylmethoxysilanes, may be prepared and used to prepare valuable silicone materials.

29 Claims, No Drawings

METHOD FOR PREPARING ORGANOSILICON COMPOUNDS FROM ELEMENTAL SILICON AND HYDROCARBON ETHERS

BACKGROUND OF THE INVENTION

This invention relates to the preparation of organosilicon compounds. In particular this invention relates to a method for the preparation of organosilicon compounds, and more particularly hydrocarbonhydrocarbonoxy silicon compounds, by the reaction of elemental silicon with hydrocarbon ethers.

The preparation of organoorganoxysilanes by the reaction of organometallic reagents with organoxysilanes has been known for over 100 years, but today's commercial silicone production is based on the more economical direct process reaction of organic halides, particularly methyl chloride, with various forms of metallic silicon at high temperature to produce organohalosilanes. From several points of view, such as minimum corrosion of processing equipment and by-product handling, organoorganoxysilanes are preferred over organohalosilanes as intermediates for the production of silicones. Consequently, a commercially attractive method for the production of organoorganoxysilanes is needed.

Rochow, U.S. Pat. No. 2,459,539 has reacted dialkyl ethers with silicon at elevated temperatures in the presence of a hydrogen halide to prepare alkyl-substituted halogenosilanes but not alkyl-substituted alkoxysilanes. This route to organosilicon compounds thus suffers many of the disadvantages of the aforesaid direct process route to organohalosilanes.

Bonitz, U.S. Pat. No. 3,505,379 discloses a process for preparing alkyl-substituted alkoxysilanes which avoids organochlorosilanes but which requires a hydrosilylation reaction. In addition to being a more expensive two-step process, the invention of Bonitz is not useful for preparing the commercially important methyl-substituted alkoxysilanes.

Yamada, et al., Japanese Pat. No. 187,342 have described the reaction of alkyl and aryl ethers with metallic silicon at atmospheric pressure in a flow-through, hot tube system to produce alkylalkoxysilanes and arylalkoxysilanes. Although very high temperatures were needed, it was theorized therein that alloying the metallic silicon with copper, silver, reduced copper or reduced silver could allow the reaction temperature to be reduced and the yield of product to be increased.

The method of Yamada, et al. has not been adopted as a method for the commercial production of silicone intermediates, in spite of its attractiveness. Although many reasons undoubtedly exist for this non-adoption, a main deterrent to its adoption may be the work of Zuckerman, Ph.D. Thesis, Harvard University, 1960, which concluded that the reaction of ethers with silicon as stated by Yamada, et al. does not produce organosilicon compounds. Furthermore, Newton, et al. *Inorg. Chem.* 9, 1072 (1971) failed to produce methylmethoxysilanes from the reaction of dimethyl ether with a silicon-copper alloy in a silicone oil slurry.

In spite of these negative results, the desirability of preparing organosilicon compounds directly from silicon and hydrocarbon ethers spurred the following invention.

SUMMARY OF THE INVENTION

It is an object of this invention to provide an improved method for preparing organosilicon compounds using elemental silicon and hydrocarbon ethers.

It is another object of this invention to provide a one-step method for preparing hydrocarbonhydrocarbonoxy silicon compounds from elemental silicon and hydrocarbon ethers at relatively low temperatures.

These and other objects will be obvious after considering the following disclosure and appended claims which disclose a method comprising heating, in confinement, an activated silicon alloy with a hydrocarbon ether in the presence of a halogen-containing catalyst to prepare silicon compounds bearing hydrocarbon groups and hydrocarbonoxy groups. The reaction proceeds at low temperature, compared to the temperature of known methods for reacting hydrocarbon ethers directly with silicon.

Without limiting the invention, it is theorized that the method of this invention succeeds where other methods have failed because of the use of a halogen-containing catalyst and because of the use of a closed system to insure the continuing cooperative interaction of activated silicon, hydrocarbon ether and halogen-containing catalyst.

DESCRIPTION OF THE INVENTION

This invention relates to a method for preparing organosilicon compounds, said method comprising contacting components consisting essentially of an activated silicon a hydrocarbon ether wherein at least one oxygen-bonded carbon atom is an aliphatic carbon atom and a catalytic amount of a halogen-containing catalyst, said contacting being done in a closed container at a temperature of at least approximately 200° C., thereby producing at least one organosilicon compound bearing at least one silicon-bonded hydrocarbon radical and at least one silicon-bonded hydrocarbonoxy radical.

Any activated elemental silicon is suitable for the method of this invention. For example, either silicon alloys or hyper-pure silicon are suitable for use in this method, when activated; however, silicon alloys are preferred. Preferred silicon alloys are activated commercial metallurgical alloys which contain at least 95 weight percent silicon and up to 5 weight percent other elements such as Na, K, Mg, Ca, Fe, Ag, Zn, Al, Sn, B, P, O, S, Cu, V, Cr, Co, Sb, Bi, As, Zr, Ti, and Pb. Activated commercial ferrosilicon alloys containing 30 weight percent iron and calcium-silicon alloys containing 27 percent calcium are satisfactory for the method of this invention. Higher or lower levels of iron or calcium may also be suitable.

Commercial silicon alloys, as well as hyperpure silicon, are essentially inert in the method of this invention unless they are activated. Activation of the silicon is done by impregnating the silicon with certain activating elements. One method for activating silicon entails melting the silicon with certain elements, permitting the melt to solidify and grinding the resulting solid to a fine powder. Alternately, an intimate mixture of silicon powder and certain elements may be heated and/or ground. It is believed that said elements diffuse into the particles of silicon during said heating and/or grinding. In yet another method for activating silicon, salts of certain elements are reduced, in intimate mixture with the silicon, either by reaction in aqueous solution or by heating. It is believed that said elements so formed in the reducing process physically combine with the particles of silicon, such as by deposition onto the silicon and diffusion into the silicon.

Elements and salts which are effective impregnants for activating silicon by the methods described above include the metals of Group IB and IIB of the periodic table of elements, and their salts, i.e. Cu, Ag, Au, Zn, Cd, Hg and their salts such as oxides, sulfates, halides, nitrates, phosphates, and carbonates. These are most effective for activating silicon when iron, aluminum and other elements are present in the silicon. The activating effect of the Group IB or IIB metals and salts is also increased if more than one of said groups is used simultaneously or sequentially in the above activation methods. Preferred combinations of activating elements are copper and tin, copper and mercury, and copper, tin and mercury.

The exact nature of the activated silicon is not completely known but it is believed that the silicon exists as small crystalline phases surrounded by phases which are rich in said elements other than silicon.

The hydrocarbon ethers which are operative in the method of this invention are any hydrocarbon ethers having at least one aliphatic oxygen-bonded carbon atom, thereby excluding diaryl ethers having only aromatic oxygen-bonded carbon atoms such as diphenyl ether. Examples of suitable ethers include alkyl ethers such a dimethyl ether, dibenzyl ether, diethyl ether, dipropyl ether, methylbenzyl ether, methylethyl ether, methylvinyl ether, and methylallyl ether; and aralkyl ethers such as methylphenyl ether, ethylphenyl ether, methyltolyl ether and benzylphenyl ether.

Preferred hydrocarbon ethers have the formula ROR wherein R denotes a monovalent hydrocarbon radical having from 1 to 10 carbon atoms selected from the group consisting of primary alkyl radicals such as methyl, ethyl, n-propyl, n-butyl, i-butyl, 2,3-dimethylbutyl, n-octyl, i-octyl, and n-decyl, alkenyl radicals such as vinyl and allyl, aryl radicals such as phenyl and tolyl and primary aralkyl radicals such a benzyl and phenethyl. At least one R radical in ROR is not an aryl radical. Hydrocarbon ethers of the formula ROR are preferred for the preparation of less complex mixtures of products and commercially desired hydrocarbonhydrocarbonoxysilanes and siloxanes. Hydrocarbon ethers not having the formula ROR are less preferred since they may lead to more complex mixtures of products comprising less desirable but still useful organosilicon compounds.

Dimethyl ether is a highly preferred hydrocarbon ether in the method of this invention for several reasons. In the first place dimethyl ether will provide commercially desired methyl- and methoxy-containing silicon compounds. Additionally, dimethyl ether is an inexpensive and readily available methyl-containing ether. Also, in view of the plurality of possible organosilicon compounds obtainable from mixed ethers dimethyl ether is to be preferred for leading to more easily purified mixtures containing fewer and simpler organosilicon compounds.

Diethyl ether is another highly preferred hydrocarbon ether in the method of this invention since it affords high yields of product, similar to dimethyl ether. Higher dialkyl ethers afford lower yields of product in the method of this invention.

The halogen-containing catalyst is any active source of halide, preferably chloride or bromide. By active source it is meant a halogen-containing compound which will react with the hydrocarbon ether to produce an aliphatic halide or which will react with the activated silicon to produce a silicon halide or which is a silicon halide or an aliphatic halide.

Examples of halogen-containing catalysts include silicon halides such as halosilanes such as $SiCl_4$, $CH_3SiCl_3$, $(CH_3)_2SiCl_2$ and $(CH_3)_3SiCl$ and halosiloxanes such as $Cl_3SiOSiCl_3$ and $Cl(CH_3)_2SiOSi(CH_3)_2Cl$, aliphatic halides such as alkyl halides such as $CH_3Br$ and $CH_3CH_2Br$, alkylene halides such as $CH_2Cl_2$, $CH_2Br_2$ and $BrCH_2CH_2Br$, alkenyl halides such as $CH_2{=}CHCl$ and $CH_2{=}CHCH_2Br$ and cycloaliphatic halides such as cyclohexyl bromide, hydrogen halides such as HCl and HBr, and metal halides such as $CuCl_2$, $Cu_2Cl_2$, $ZnBr_2$, $CuBr_2$, and $HgBr_2$.

It is believed that in the method of this invention the catalyst is or gives rise to an aliphatic halide which reacts with activated silicon to produce a silicon halide which reacts with hydrocarbon ether to yield replacement aliphatic halide thereby completing the catalyst cycle. Aliphatic halide is recoverable from the reaction mixture.

Bromide-containing catalysts and especially aliphatic bromides seem to be most effective in the method of this invention and are highly preferred. Aliphatic fluorides and iodides seem to be least effective.

The method of this invention may be practiced in any suitable manner, it being only required to contact the activated silicon, hydrocarbon ether and halogen-containing catalyst in a closed system for a sufficient length of time at a temperature of at least approximately 200° C. in order to produce hydrocarbonhydrocarbonoxy silicon compounds. By a closed system, it is meant a reaction vessel and any associated means that will insure the contacting of the silicon, ether and catalyst under at least autogeneous pressure for a suitable length of time at a suitable reaction temperatures. The reaction mixture may further contain an inert liquid such as mineral oil or decalin to facilitate better contact between the reactants before and during the reaction.

In one example of the invention the components may be mixed at a temperature below their boiling points, the mixture placed into a sealable reaction vessel, the reaction vessel sealed and the components heated to a temperature of at least approximately 200° C. for a suitable period of time. Alternately the activated silicon may be placed into a reaction vessel which is sealably equipped for the introduction of the hydrocarbon ether and halogen-containing catalyst, the activated silicon heated to a suitable reaction temperature and the remaining components introduced into the reaction vessel with suitable pressure for a suitable length of time. Other suitable techniques will be obvious to the reader. In any case, the pressure within the reaction vessel will be due to the vapor pressure of the components at the temperature used, i.e. autogeneous pressure.

The reaction proceeds readily at temperatures above approximately 200° C., but the temperature used during the contacting of the reactants should not be so high as to decompose the desirable products formed thereby. The reaction is conveniently conducted at a temperature of from 200° to 300° C. and for a length of time of from approximately 1 to 100 hours, said time generally being inversely related to the reaction temperature. More or less reaction time may be suitable under certain conditions of silicon activity, catalyst effectiveness and hydrocarbon ether reactivity.

In view of the hydrolyzable nature of the silicon-alkoxy bond it is preferred to avoid more than trace amounts of water in the reaction mixture during the contacting step of this invention.

The components may be contacted in any suitable amounts commensurate with the size of the reaction vessel. Preferably the amount of hydrocarbon ether, expressed in molar parts, that is contacted with the activated silicon is greater than the amount of silicon in said activated silicon, expressed in atom parts. That is to say, the ratio of the molar parts of hydrocarbon ether to atom parts of silicon has a value of more than 1 such as 1.01, 1.1, 1.5, 2.0, 3.0, 4.0, 5.0, 10.0, and more. Reaction mixtures wherein said ratio is less than 1 are also suitable for the method of this invention, however, the resulting product of such a mixture is prone to be insoluble and sometimes almost intractible.

The amount of halogen-containing catalyst to be used in the method of this invention is merely a catalytic amount, i.e. and amount which will permit the reaction to proceed at a desirable rate. The amount of catalyst is conveniently expressed as the ratio of molar parts of catalyst to atom parts of silicon, which ratio may have a value of from 0.001 to 1.0, preferably from 0.01 to 0.1.

After the reaction is complete the products may be recovered by any suitable method such as by filtration, extraction, distillation, evaporation and decantation. Purification of the products may be accomplished by well-known methods such as fractionation, chromatography, and the like.

The organosilicon products of the method of this invention bear at least one silicon-bonded hydrocarbon radical and at least one silicon-bonded hydrocarbonoxy radical per molecule. The silicon-bonded hydrocarbon radicals and hydrocarbonoxy radicals of the organosilicon product are derived from the hydrocarbon ether. It has been observed that any aryl portion of the ether, i.e. a portion linked to the ether oxygen by an aromatic carbon, will be found in the organosilicon compound only as an hydrocarbonoxy moiety, whereas a non-aryl portion of the ether may be found in the organosilicon compound as a hydrocarbon moiety and/or as a hydrocarbonoxy moiety. For example, methyl phenyl ether will give rise to organosilicon compounds bearing methyl radicals and phenoxy radicals whereas benzylmethyl ether will give rise to organosilicon compounds bearing methyl and/or benzyl radicals along with methoxy and/or benzyloxy radicals.

The products of the method of this invention may be monomeric, i.e. bearing one silicon atom per molecule, and/or polymeric, i.e. bearing more than one silicon atom per molecule. Polymeric organosilicon compounds have their silicon atoms joined by divalent oxygen atoms.

Products of the method of this invention are silanes and siloxanes which respond to the average unit formula

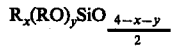

when the hydrocarbon ether reactant responds to the formula ROR. R denotes a monovalent hydrocarbon radical hereinbefore defined with the exception that no aryl radical is directly bonded to silicon by way of an aromatic carbon atom. In a highly preferred method of this invention $CH_3OCH_3$ will provide methylmethoxysilanes and methylmethoxysiloxanes of the average unit formula

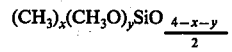

Herein $x$ and $y$ independently have an average value of from greater than zero to three, for example 0.01, 0.1, 0.5, 1.0, 1.5, 1.9, 2.1, 2.6, and 3.0, with the limitation that the total of $x + y$ has a value which does not exceed 4.0.

Examples of silanes obtained from ethers of the formula ROR, wherein $x + y = 4$, include $R(RO)_3Si$ such as $CH_3(CH_3O)_3Si$, $CH_3CH_2(CH_3O)_3Si$, $CH_3(C_6H_5O)_3Si$, $CH_3(CH_3CH_2O)_3Si$, $CH_3(C_6H_5CH_2O)_3Si$, $CH_2=CHCH(CH_3O)_3Si$, $CH_3CH_2(CH_3CH_2O)_3Si$, $CH_3(CH_3O)_2(CH_3CH_2O)Si$, and $C_6H_5CH_2(CH_3O)_2(C_6H_5CH_2O)Si$; $R_2(RO)_2Si$ such as $(CH_3)_2(CH_3O)_2Si$, $(CH_3)_2(C_6H_5O)_2Si$, $(CH_3CH_2)_2(CH_3CH_2O)_2Si$, $(CH_3)(C_6H_5CH_2)(CH_3O)(C_6H_5CH_2O)Si$ and $(C_6H_5CH_2)_2(CH_3O)_2Si$; and $R_3(RO)Si$ such as $(CH_3)_3(CH_3O)Si$, $(CH_3CH_2)_3(CH_3CH_2O)Si$ and $(CH_3)_2(C_6H_5CH_2)(C_6H_5CH_2O)Si$. Examples of siloxanes obtained from ethers of the formula ROR, wherein $x + y < 4$, include disiloxanes such as $R_2(RO)Si-OSi(OR)_3$ such as $(CH_3)_2(CH_3O)SiOSi(OCH_3)_3$ and $R(RO)_2SiOSi(OR)_2R$ such as $CH_3CH_2CH_2(CH_3CH_2CH_2O)_2Si-OSi(OCH_2CH_2CH_3)_2(CH_2CH_2CH_3)$, trisiloxanes such as $R_3SiO(R_2SiO)_2R$, $RO(R_2SiO)_3OR$, $(ROSiR_2O)_2RSiOR$ and $R(RO)_2SiO(R)(RO)SiOSi(OR)_2R$, and higher siloxanes such as $RO(R_2SiO)_4OR$, wherein R is a defined hereinabove.

Theoretically the number of silicon-bonded hydrocarbon radicals should equal the number of silicon-bonded hydrocarbonoxy radicals in the product of this method, but there occurs in the reaction a loss of some silicon-bonded hydrocarbonoxy radicals, undoubtedly leading to the formation of the observed siloxanes. Consequently the number of silicon-bonded hydrocarbon radicals usually exceeds the number of silicon-bonded hydrocarbonoxy radicals in the product. This loss of silicon-bonded hydrocarbonoxy radicals is not extensive however since the molar amounts of silanes usually exceeds the molar amount of siloxanes in the product.

The method of this invention is useful for providing reactive hydrocarbonhydrocarbonoxy silicon compounds which may be isolated in pure form and converted to other silicon compounds such as well-known, valuable silicone materials such as fluids, gums and resins in well-known processes. The reaction products may also be separated from unreacted starting materials and directly converted to silicone products by well-known techniques, such as hydrolysis, condensation and endblocking, without further purification.

Having described the invention the following examples are offered to further illustrate and not to limit the invention which is properly delineated by the appended claims. It is believed at this time that the best way to practice this invention is illustrated by these examples.

All ether/silicon ratios and catalyst/silicon ratios are ratios of molar parts to atom parts.

EXAMPLE 1

A metallurgical grade silicon powder, 150 g., was ground to an average particule size of 2.74μm. in a steel ball mill (Norton Model 611, size 00) for 16 hours with 12 g. of copper powder, 300 ml. of hexane and 826 g. of stainless steel grinding balls. The metallurgical grade silicone was analyzed to be, by weight, >98 percent Si, 0.44 percent Fe, 0.26 percent Al, 0.058 percent Ca, 0.005 percent Sn, 0.04 percent Mn, 0.032 percent Ti, 0.015 percent V, 0.002 percent B, 0.014 percent Cr, 0.05 percent Zn and 0.002 percent Pb. The ground activated silicon alloy was found to comprise, for every 100 atom parts of silicon, 3.3 atom parts of copper, 0.3 atom parts of iron, 0.43 atom parts of aluminum and 0.13 atom parts of calcium. Other elements were not analyzed.

A 300 ml. steel autoclave was charged with a mixture of a portion of the activated silicon alloy and approximately 350 molar parts of dimethyl ether and 1 molar part of methyl bromide for every 100 atom parts of silicon in the alloy charged to the autoclave. The sealed autocalve was heated under autogeneous pressure for 20 hours at 258° C., then cooled and its contents were extracted with a known quantity of benzene to separate soluble materials from insoluble residues. The benzene extract was analyzed by gas-liquid chromatography to indicate the amount of each volatile component in the extract, relative to benzene. The extract was also analyzed by nuclear magnetic resonance to indicate the amount of Si—$CH_3$ groups and Si—$OCH_3$ groups in the extract, relative to benzene. From these data the equivalents of Si—$CH_3$ groups and of Si—$OCH_3$ groups per atom part of charged silicon were calculated and converted to equivalent percent (E%) as follows:

$$E\% \text{ (SiCH}_3) = \frac{\text{equivalents of Si}-\text{CH}_3 \times 100}{\text{atom parts of Si}} = 106$$

$$E\% \text{ (SiOCH}_3) = \frac{\text{equivalents of Si}-\text{OCH}_3 \times 100}{\text{atom parts of Si}} = 74$$

EXAMPLE 2

The metallurgical grade silicon powder of Example 1, 150 g., was ball-milled with 13 g. of copper powder, 1.5 g. of tin powder, 3 g. of mercury and 300 ml. of hexane, as above, to give rise to an activated silicon alloy having, for every 100 atom parts of Si, the indicated atom parts of at least each element: 3.4 of Cu, 0.22 of Fe, 0.43 of Al, 0.13 of Ca, 0.25 of Hg and 0.21 of Sn. Other elements were not analyzed.

A 300 ml. autoclave was charged with a mixture of alloy, approximately 350 molar parts of dimethyl ether and 10 molar parts of methyl bromide for every 100 atom parts of silicon in the alloy that was charged into the autoclave. The sealed autoclave was heated under autogeneous pressure for 16 hours at 262° C. and its contents were analyzed as in Example 1 to give E% ($SiCH_3$) = 130 and E% ($SiOCH_3$) = 65.

The experiment was repeated with decalin added to the reaction mixture. The sealed autoclave was heated to 266° C. for 17 hours and its contents were analyzed, as above, to give E% ($SiCH_3$) = 160 and E% ($SiOCH_3$) = 89.

EXAMPLE 3

A silicon alloy powder having an average particle size of 2.82 μm and having been previously heated for 10 hours at 300° C. in the presence of methyl chloride was washed with hexane, dried and analyzed to contain by weight, 5.5 percent Cu, 3.3 percent Fe, 2.9 percent Al, 0.27 percent Ca, 0.05 percent Zn, 0.01 percent Sn, 1.5 percent Cl and the balance Si. This catalyzed alloy was heated at 262° C. for up to 50 hours in sealed glass ampoules with 10 molar parts of dimethyl ether for every 1 atom part of Si in the activated alloy. Analysis of the reaction mixture, as in Example 1, showed a gradual increase in the values of E% ($SiCH_3$) from 40 at 4 hours to approximately 80 at 50 hours and of E% ($SiOCH_3$) from 20 to 4 hours to approximately 60 to 50 hours.

EXAMPLE 4

The activated, catalyzed silicon alloy of Example 3 was heated in sealed glass ampoules for 16 hours at 260° C. with dimethyl ether and additional catalyst. Table I summarizes the parameters of the experiment and the results obtained.

TABLE I

| $(CH_3)_2O/Si$ | Additional Catalyst (Catalyst/Si) | E% $SiCH_3$ | E% $SiOCH_3$ |
|---|---|---|---|
| 26.3[a] | $CH_3Br$ (0.53) | 150 | 70 |
| 14.4 | $(CH_3)_2SiCl_2$ (0.12) | 70[b] | 40[b] |
| 3.1 | $CH_3Cl$ (0.09) | 50 | (c) |
| 2.1 | $CH_3Br$ (0.06) | 130 | (c) |

[a]Mineral oil also present
[b]Temperature was 270° C. instead of 260° C.
[c]Not measured

EXAMPLE 5

The activated, catalyst silicon alloy of Example 3 was reacted with dimethyl ether under various conditions in sealed glass ampoules. These reactions are summarized in Table II. Products were isolated by gas-phase chromatography and identified by nuclear magnetic resonance and mass spectroscopy.

TABLE II

| Reaction Conditions | Exp 5-1 | Exp 5-2 | Exp 5-3 |
|---|---|---|---|
| Temperature, ° C. | 260 | 272 | 261 |
| Time, Hours | 15 | 15 | 6 |
| $(CH_3)_2O/Si$ | 0.78 | 1.09 | 1.83 |
| $CH_3Br/Si$ | 0 | 0 | .08 |
| Mineral Oil | 0 | 0 | .003 |
| E% (Product) | | | |
| $(CH_3)_3Si(OCH_3)$ | 3 | 5.4 | (a) |
| $(CH_3)_2Si(OCH_3)_2$ | 12.8 | 18.2 | 64.4 |
| $(CH_3)Si(OCH_3)_3$ | 1.1 | 16.0 | (a) |
| $(CH_3)_2CH_3OSiOSi(CH_3)_3$ | 0.9 | (a) | (a) |
| $(CH_3)_3SiO\{(CH_3)_2SiO\}_2CH_3$ | 3.5 | 4.9 | (a) |
| $CH_3O\{(CH_3)_2SiO\}_3CH_3$ | 8.4 | 8.4 | (a) |
| $\{(CH_3)_2CH_3OSi\}_2Si(CH_3)OCH_3$ | 2.0 | 0.4 | (a) |
| $CH_3O\{(CH_3)_2SiO\}_4CH_3$ | 3.2 | 2.4 | (a) |
| $CH_3O\{(CH_3)_2SiO\}_2Si(CH_3)(OCH_3)OSi(CH_3)_2OCH_3$ | 2.1 | 0.7 | (a) |

[a]Not Measured

EXAMPLE 6

The activated catalyzed silicon alloy of Example 3 was reacted with various symmetrical alkyl ethers for 16 hours at 255° ± 5° C. in sealed glass ampoules. Table III summarizes these experiments.

Products from diethyl ether included $Et_2Si(OEt)_2$, $EtSi(OEt)_3$, $\{EtSi(OEt)_2\}_2O$ and $\{EtSi(OEt)_2O\}_2SiEt(OEt)$ where Et denotes the ethyl radical.

Products from di-n-propyl ether included $Pr_2Si(OPr)_2$, $PrSi(OPr)_3$, $Pr_2(PrO)SiOSi(OPr)_2Pr$ and $\{PrSi(OPr)_2\}_2O$ where Pr denotes the n-propyl radical.

Products from di-i-amyl ether included $Am_2Si(OAm)_2$, $AmSi(OAm)_3$ and $\{AmSi(OAm)_2\}_2O$ where Am denotes the isoamly radical.

TABLE III

| Ether | Ether/Si | Additional Catalyst | Additional Catalyst/Si | E% SiR | E% SiOR |
|---|---|---|---|---|---|
| Diethyl | 2.67 | None | 0 | 3 | 3 |
|  | 2.23 | $CH_3CH_2Br$ | .02 | 14 | 13 |
|  | 2.73 | $CH_3CH_2Br$ | .02 | 118 | 92 |
| Di-n-propyl | 1.69 | None | 0 | nil | nil |
|  | 1.69 | $CH_3CH_2Br$ | 0.14 | 78 | 60 |
|  | 1.72 | $ZnBr_2$ | 0.01 | 112 | 58 |
| Di-i-amyl | 0.94 | None | 0 | nil | nil |
|  | 0.96 | $CH_3Br$ | 0.07 | (a) | 41 |
|  | 0.98 | $CH_3Br$ | 0.07 | (a) | 42 |

(a)Present

EXAMPLE 7

Example 6 was repeated with various asymmetrical ethers. A mixture of benzylmethyl ether (ether/Si = 2.3) and benzyl chloride (catalyst/Si = 0.05) heated at 219° C. for 16 hours, produced $C_6H_5CH_2Si(OCH_3)_3$, $(C_6H_5CH_2)_2Si(OCH_3)_2$ and $CH_3Si(OCH_3)_3$ among others. A mixture of allylmethyl ether (ether/Si = 1.68), benzene (solvent/Si = 2.47) and $CH_3Br$ (catalyst/Si = 0.04), heated at 254° C. for 21 hours, produced E% $SiCH_3$ = 23, E% $SiOCH_3$ = 73 and E% $SiCH_2CH=CH$ >E% $SiCH_3$. Methylphenyl ether results are summarized in Table IV. No evidence to support silicon-phenyl bond formation was obtained. Predominant silicon-containing compounds were $(CH_3)_2Si(OC_6H_5)_2$ and $CH_3Si(OC_6H_5)_3$.

TABLE IV

| $C_6H_5OCH_3$/Si | Additional Catalyst | Additional Catalyst/Si | Conditions | E% $SiCH_3$ | E% $SiOC_6H_5$ |
|---|---|---|---|---|---|
| 1.49 | None | 0 | 242° C/17 hr. | 17 | (a) |
| 2.29 | None | 0 | 262° C/17 hr. | 25 | (a) |
| 2.34 | None | 0 | 248° C/44 hr. | 82 | 128 |
| 1.93 | $SiCl_4$ | 0.02 | 256° C/16 hr. | 85 | (a) |
| 2.06 | $SiCl_4$ | 0.05 | 256° C/16 hr. | 109 | (a) |
| 2.06 | $ZnBr_2$ | 0.03 | 260° C/113 hr. | 116 | 174 |

(a)Not measured

EXAMPLE 8

Inactive semi-conductor grade polycrystalline silicon, was used to prepare various silicon samples. Sample 8-1 was prepared by sintering 100 atom parts of Si and 1.9 molar parts of CuO at 1072° C. in a hydrogen atmosphere. Sample 8-2 was prepared by grinding to a fine powder in a ring mill 100 atom parts of Si and from 0.9 to 4.0 atom parts of Cu. Sample 8-3 was prepared by similarly grinding 100 atom parts of Si, 3.4 atom parts of Cu and 0.23 atom parts of Sn. Sample 8-4 was prepared by similarly grinding 100 atom parts of Si and 0.28 atom parts of Sn. Sample 8-5 was prepared by grinding to a fine powder in a ball mill 100 atom parts of Si and 3.3 atom parts of Cu. Sample 8-6 was prepared by heating sample 8-5 in a hydrogen atmosphere at 1052° C. for 0.5 hr. Sample 8-7 was prepared by melting together 100 atom parts of Si, 0.05 atom parts of Al, 0.25 parts of Fe, and 0.07 atom parts of Ca. The melt was cooled and ground. Dimethyl ether and optionally, $CH_3Br$ and additional catalysts, was heated with the above alloys under various conditions in sealed glass ampoules and the products were analyzed as in Example 1. The results which are summarized in Table V shows that semi-conductor grade silicon is difficult to activate.

TABLE V

| Silicon Sample | $(CH_3)_2O$/Si | $CH_3Br$/Si | Additional Catalyst | Conditions | E% $SiCH_3$ |
|---|---|---|---|---|---|
| 8-1 | 0.49 | 0 | None | 243° C/15 hr. | Nil |
| 8-1 | 0.65 | 0 | $ZnCl_2$ | 243° C/15 hr. | Nil |
| 8-2 | 3.14 | 0.09 | None | 262° C/16 hr. | Nil |
| 8-2 | 3.14(a) | 0.09 | None | 262° C/16 hr. | Nil |
| 8-3 | 2.60 | 0.08 | None | 266° C/16 hr. | 23 |
| 8-3 | 2.60 | 0.08 | Hg | 258° C/16 hr. | 39 |
| 8-3 | 2.60(a) | 0.08 | None | 266° C/16 hr. | 32 |
| 8-4 | 2.30(a) | 0.03 | None | 250° C/16 hr. | Nil |
| 8-5 | 2.62 | 0.08 | None | 258° C/16 hr. | 0.5 |
| 8-5 | 2.62 | 0.08 | None | 258° C/16 hr. | 0.5 |
| 8-5 | 2.62 | 0.08 | $SnF_2$ | 258° C/16 hr. | 25 |
| 8-5 | 2.62 | 0.08 | KF.HF | 258° C/16 hr. | Nil |
| 8-6 | 4.09 | <0.01 | None | 259° C/16 hr. | Nil |
| 8-6 | 4.09 | <0.01 | $SnF_2$ | 259° C/16 hr. | 100 |
| 8-7 | 2.57(a) | <0.01 | $CuF_2$ + $HgBr_2$ | 253° C/16 hr. | 62 |
| 8-7 | 2.31(a) | <0.01 | $CuF_2$ + $SnF_2$ | 253° C/16 hr | 45 |

(a)Decalin was present

EXAMPLE 9

Metallurgical grade silicon described in Example 1 was used to prepare several activated silicon alloys. Sample 9-1 was prepared by shaking the powdered silicon with an aqueous solution of $CuSO_4.5H_2O$ and HF to deposit copper onto the silicon alloy. Sample 9-2 was prepared by shaking sample 9-1 with aqueous $HgCl_2$ to prepare an activated alloy having 1.8 atom parts of Cu and 0.14 atom parts of Hg for every 100 atom parts of Si. Sample 9-3 was prepared by shaking the powdered silicon with an aqueous solution of $CuSO_4.5H_2O$, HF and $SnF_2$, followed by shaking with aqueous $HgCl_2$. Sample 9-4 was prepared by heating sample 9-1 in an atmosphere of hydrogen for 50 minutes at 1000° C. Each of the resulting activated silicon alloys was washed (except sample 9-4), dried, and was heated with dimethyl ether, methyl bromide, and decalin in sealed glass ampoules. The products were analyzed as in Example 1. Results are summarized in Table VI.

TABLE VI

| Silicon Sample | $(CH_3)_2O$/Si | $CH_3Br$/Si | Conditions | E% $SiCH_3$ |
|---|---|---|---|---|
| 9-1 | 3.16 | 0.16 | 257° C/16 hr. | 30 |
| 9-2 | 3.80 | 0.16 | 257° C/16 hr. | 120 |
| 9-3 | 2.64 | 0.09 | 260° C/15 hr. | 91 |
| 9-4 | 3.32[a] | 0.09 | 258° C/18 hr. | 126 |

[a]No decalin. Trace of $HgBr_2$ added

EXAMPLE 10

Several activated silicon alloys were prepared by grinding a metallurgical grade silicon with copper and optionally, tin and mercury, in a ball mill. The metallurgical grade silicon was analyzed, by weight, as 97.5 percent Si, 0.49 percent Fe, 0.46 percent Al, 0.14 percent Ca, 0.012 percent Cu, 0.015 percent Zn, 0.01 percent Mg, 0.014 percent Mn, 0.04 percent Ti, 0.025 percent V, 0.003 percent Ni, and 0.0024 percent B. Sample 10-1 had, as atom parts of the element per 100 atom parts of Si, 4.6 of Cu, 1.0 of Hg, 0.14 of Sn, among others. Sample 10-2, similarly had 3.8 of Cu, 0.02 of Hg and 1.4 of Sn, among others. Sample 10-3, similarly, had 3.4 of Cu and 7.8 of Sn, among others. Sample 10-4, similarly, had 3.7 of Cu, among others. Sample 10-5, similarly had 3.4 of Cu, 0.25 of Hg and 0.2 of Sn, among others.

Each of the resulting activated silicon alloys was heated with dimethyl ether, methyl bromide, and decalin in sealed glass ampoules and the reaction mixture was analyzed as in Example 1. Table VII summarizes the results.

TABLE VII

| Silcon Sample | $(CH_3)_2O$/Si | $CH_3Br$/Si | Conditions | E% $SiCH_3$ |
|---|---|---|---|---|
| 10-1 | 2.28 | 0.06 | 258° C/16 hr. | 113 |
| 10-2 | 2.16 | 0.08 | 283° C/16 hr. | 147 |
| 10-3 | 2.29 | 0.08 | 266° C/16 hr. | 129 |
| 10-4 | 2.20 | 0.08 | 257° C/16 hr. | 42 |
| 10-5 | 2.40 | 0.17 | 257° C/16 hr. | 102 |
| 10-5 | 2.38 | 0.09[a] | 257° C/16 hr. | 107 |
| 10-5 | 2.50 | 0[a] | 257° C/16 hr. | Nil |

[a]No decalin

EXAMPLE 11

A ferrosilicon alloy having approximately 70.3 percent Si, 26.9 percent Fe, 1.8 percent Al, and 1 percent Ca by weight was ground to a fine powder to provide sample 11-1 which had as atom parts of each element per 100 atom parts of Si, 19.2 of Fe, 2.7 of Al, and 1.0 of Ca. Sample 11-2 having 0.13 atom parts of Cu, in addition to the above atom parts, was prepared by grinding sample 11-1 with copper powder. Sample 11-3, having 0.13 atom parts of Cu, 0.01 atom parts of Hg and 0.008 atom parts of Sn, in addition to the above atoms parts was prepared by grinding sample 11-1 with copper, mercury and tin.

Each of the resulting activated silicon alloys was heated in sealed glass ampoules with dimethyl ether, methyl bromide, and in some cases, additional halogen-containing catalyst. The reaction products were analyzed as in Example 1. The results are summarized in Table VIII.

TABLE VIII

| Silicon Sample | $(CH_3)_2O$/Si | $CH_3Br$/Si | Additional Catalyst (Catalyst/Si) | Conditions | E% $SiCH_3$ |
|---|---|---|---|---|---|
| 11-1 | 4.03 | 0 | $ZnBr_2$ (0.0004) | 220° C/16 hr. | Nil |
| 11-1 | 2.55[a] | 0.11 | $CuF_2.2H_2O$ (0.002) plus $HgBr_2$ (trace) | 257° C/16 hr. | 35 |
| 11-1 | 3.25[a] | 0.11 | $CuF_2.2H_2O$ (.0001) plus $HgBr_2$ (trace) | 257° C/16 hr. | 80 |
| 11-2 | 4.16[a] | 0.14 | None | 260° C/16 hr. | 1.3 |
| 11-2 | 3.43 | 0.12 | $HgBr_2$ (0.0002) | 260° C/16 hr. | 67 |
| 11-2 | 3.28 | 0.12 | $SnF_2$ (0.0008) | 260° C/16 hr. | 31 |
| 11-3 | 5.23[a] | 0.12 | None | 260° C/16 hr. | 64 |
| 11-3 | 4.49 | 0.12 | None | 260° C/16 hr. | 43 |
| 11-3 | 4.58[a] | 0.12 | None | 260° C/16 hr. | 70 |

[a]Decalin present

EXAMPLE 12

A calcium-silicon alloy having approximately 65.02 percent Si, 27.48 percent Ca, 6.25 percent Fe, and 1.25 percent Al by weight was ground to a fine powder to provide sample 12-1 which had, as atom parts of each element per 100 atom parts of Si, 29.5 of Ca, 4.8 of Fe and 2.0 of Al. Sample 12-2 was prepared by stirring sample 12-1 with an aqueous solution of $CuSO_4.5H_2O$ and HF to deposit copper on the alloy. Sample 12-3 was prepared by grinding 12-1 with copper, tin and mercury.

Each of the resulting activated silicon alloys was heated in sealed glass ampoules with dimethyl ether and catalyst. The reaction products were analyzed as in Example 1. The results are summarized in Table IX.

TABLE IX

| Silicon Sample | $(CH_3)_2O$/Si | Catalyst (Catalyst/Si) | Conditions | E% $SiCH_3$ |
|---|---|---|---|---|
| 12-1 | 4.26 | $ZnBr_2$ (0.0004) | 217° C/16 hr. | Nil |
| 12-2 | 3.81 | $CH_3Br$ (0.13) | 257° C/16 hr. | 12 |
| 12-3 | 4.70 | $CH_3Br$ (0.13) | 259° C/16 hr. | 4 |

The following example illustrates the failure of dimethyl ether to react with silicon in the absence of a closed system.

EXAMPLE 13

This example is given for comparison. Gaseous dimethyl ether was passed through a fixed bed of powdered silicon in a stainless steel tube heated by an oven.

The tube was packed with a silicon-copper alloy which was prepared by heating an intimate mixture of powdered metallurgical grade silicon and cuprous chloride to 350° in the tube. During this period of heating at 350° silicon tetrachloride formed. Dimethyl ether was introduced at one end of the tube at various rates but usually at such a rate as to give a calculated period of contact with the silicon of about 2 minutes. Vapors leaving the second end of the tube were condensed at −78° C. and analyzed periodically by gas chromatography. The temperature of the bed of silicon was varied between 200° and 485° C. Under these conditions the condensate was unchanged dimethyl ether. Higher boiling materials were not detected.

Methyl alcohol was added as a small fraction of the dimethyl ether gas stream. Trimethoxysilane was then found in the condensate in an amount corresponding to that required for the equation 3MeOH + Si→ (MeO)$_3$SiH + H$_2$. No products were found that might be ascribed to a reaction of dimethyl ether.

1,2-Dibromoethane was added to the dimethyl ether feed. Methylbromide appeared in the condensate. A series of various organic bromides were introduced in the same manner. In each case methyl bromide was detected in the condensate, but no organosilicon compounds were detected.

Anhydrous hydrogen chloride introduced in the stream of dimethyl ether formed trace quantities of methyl chlorosilanes.

Similar experiments were repeated with the tube packed with differing grades of silicon mixed with metals and salts as catalysts for reactions with dimethyl ether. Zinc bromide caused formation of methyl bromide. Aluminum and aluminum methoxide converted some of the ether to dimethoxymethane. In no case were products found that might have resulted from chemical reaction between silicon and dimethyl ether.

That which is claimed is:

1. A method for preparing organosilicon compounds, said method comprising contacting components consisting essentially of
    (a) activated silicon
    (b) a hydrocarbon ether wherein at least one oxygen-bonded carbon atom is an aliphatic carbon atom, and
    (c) a catalytic amount of a halogen-containing catalyst, said contacting being done in a closed container at a temperature of at least approximately 200° C., thereby producing at least one organosilicon compound bearing at least one silicon-bonded hydrocarbon radical and at least one silicon-bonded hydrocarbonoxy radical.

2. A method according to claim 1 wherein the molar parts of the hydrocarbon ether is greater than the atom parts of silicon in the activated silicon during said contacting.

3. A method according to claim 2 wherein the contacting is done at autogenous pressure and at a temperature of from approximately 200° to approximately 300° C.

4. A method according to claim 3 wherein at least one organosilicon compound is recovered after said contacting.

5. A method according to claim 4 wherein an inert liquid is present during said contacting.

6. A method according to claim 1 wherein the silicon is activated with copper and at least one other element selected from the group consisting of Group IB and IIB periodic chart elements.

7. A method according to claim 6 wherein the silicon is activated with copper and tin.

8. A method according to claim 7 wherein the silicon is activated with copper, tin, and mercury.

9. A method according to claim 8 wherein the hydrocarbon ether is dimethyl ether or diethyl ether, the molar parts of said hydrocarbon ether being greater than the atom parts of silicon in said activated silicon during said contacting.

10. A method according to claim 9 wherein the contacting is done at autogeneous pressure and at a temperature of from approximately 200° to approximately 300° C.

11. A method according to claim 10 wherein at least one organosilicon compound is recovered after said contacting.

12. A method according to claim 11 wherein an inert liquid is present during said contacting.

13. A method according to claim 1 wherein the hydrocarbon ether has the formula ROR, wherein R denotes a monovalent hydrocarbon radical having from 1 to 10 carbon atoms, both inclusive.

14. A method according to claim 13 wherein the hydrocarbon ether is dimethyl ether or diethyl ether.

15. A method according to claim 14 wherein the molar parts of hydrocarbon ether is greater than the atom parts of silicon in the activated silicon during said contacting.

16. A method according to claim 15 wherein the contacting is done at autogeneous pressure and at a temperature of from approximately 200° to approximately 300° C.

17. A method according to claim 16 wherein at least one organosilicon compound is recovered after said contacting.

18. A method according to claim 17 wherein an inert liquid is present during said contacting.

19. A method according to claim 1 wherein the halogen-containing catalyst is a bromine-containing catalyst.

20. A method according to claim 19 wherein the bromine-containing catalyst is an aliphatic bromide.

21. A method according to claim 20 wherein the hydrocarbon ether is dimethyl ether or diethyl ether and the catalyst is methyl bromide, the molar parts of said hydrocarbon ether being greater than the atom parts of silicon in said activated silicon during said contacting.

22. A method according to claim 21 wherein said contacting is done at autogeneous pressure and at a temperature of from approximately 200° to approximately 300° C.

23. A method according to claim 22 wherein at least one organosilicon compound is recovered after said contacting.

24. A method according to claim 23 wherein an inert liquid is present during said contacting.

25. A method according to claim 1 wherein the organosilicon compound has the average unit formula

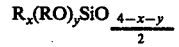

wherein R denotes a monovalent hydrocarbon radical having from 1 to 10 carbon atoms, both inclusive, the R radical which is bonded directly to silicon having an aliphatic carbon atom, $x$ has an average value of from greater than 0 to 3, $y$ has an average value of from greater than 0 to 3, the total value of $x + y$ not exceeding 4.

26. A method according to claim 25 wherein each R is methyl or ethyl.

27. A method according to claim 26 wherein the organosilicon compound comprises silanes wherein the total of $x + y = 4$.

28. A method according to claim 27 wherein (CH$_3$)$_2$SI(OCH$_3$)$_2$ is produced.

29. A method according to claim 27 wherein (CH$_3$CH$_2$)$_2$SI(OCH$_2$CH$_3$)$_2$ is produced.

* * * * *

UNITED STATES PATENT AND TRADEMARK OFFICE
CERTIFICATE OF CORRECTION

Page 1 of 2

PATENT NO. : 4,088,669
DATED : May 9, 1978
INVENTOR(S) : James R. Malek, et al.

It is certified that error appears in the above-identified patent and that said Letters Patent are hereby corrected as shown below:

Column 4, line 38, "temperatures" should read --temperature--.

Column 5, line 20, "and" should read --an--.

Column 6, line 14, the formula "$CH_3(C_6H_5CH_2O)_3Si$" should read --$CH_3(C_6H_5CH_2O)_3Si$--.

Column 6, line 20, the formula should read
--$(CH_3)(C_6H_5CH_2)(CH_3O)(C_6H_5CH_2O)Si$--.

Column 6, line 31, the formula "$R(RO)_2SiO(R)(RO)SiOSI(OR)_2R$" should read --$R(RO)_2SiO(R)(RO)SiOSi(OR)_2R$--.

Column 10, Table V, ninth line, under the heading "Additional Catalyst" the entry "None" should read --$HgBr_2$-- and under the heading "E% $SiCH_3$" the entry "0.5" should read --36--.

Column 10, Table V, the eleventh line, under the heading "Additional Catalyst" the entry "KF.HF" should read --KF·HF--.

Column 14, Claim 16, after "200°" insert --C--.

UNITED STATES PATENT AND TRADEMARK OFFICE
CERTIFICATE OF CORRECTION

PATENT NO. : 4,088,669

DATED : May 9, 1978

INVENTOR(S) : James R. Malek, et al.

It is certified that error appears in the above—identified patent and that said Letters Patent are hereby corrected as shown below:

Column 14, Claim 28, the formula should read
-- $(CH_3)_2Si(OCH_3)_2$ --.

Column 14, Claim 29, the formula should read
-- $(CH_3CH_2)_2Si(OCH_2CH_3)_2$ --.

Signed and Sealed this

Fourth Day of November 1980

[SEAL]

Attest:

SIDNEY A. DIAMOND

Attesting Officer

Commissioner of Patents and Trademarks